United States Patent
Santoro et al.

(10) Patent No.: US 6,392,100 B1
(45) Date of Patent: May 21, 2002

(54) 2-CYCLOPENTEN-1-ONE AS INHIBITORS OF THE NF-KB FACTOR

(75) Inventors: Maria Gabriella Santoro, Avellino; Antonio Rossi, Colledimacine; Giuliano Elia, Palestrina, all of (IT)

(73) Assignee: Consiglio Nazionale Delle Richerche, Rome (IT)

( * ) Notice: Subject to any disclaimer, the term of this patent is extended or adjusted under 35 U.S.C. 154(b) by 0 days.

(21) Appl. No.: 09/319,743

(22) PCT Filed: Dec. 11, 1997

(86) PCT No.: PCT/EP97/06930

§ 371 Date: Jun. 10, 1999

§ 102(e) Date: Jun. 10, 1999

(87) PCT Pub. No.: WO98/25593

PCT Pub. Date: Jun. 18, 1998

(30) Foreign Application Priority Data

Dec. 13, 1996  (IT) ........................................ RM96A0867

(51) Int. Cl.⁷ ........................ C07C 49/537; A61K 31/12
(52) U.S. Cl. ........................ 568/379; 514/690; 514/886
(58) Field of Search ................................ 514/690, 886; 562/503; 560/121; 568/379, 380

(56) References Cited

U.S. PATENT DOCUMENTS

| | | |
|---|---|---|
| 5,116,869 A | 5/1992 | Sugiura et al. |
| 5,216,183 A | 6/1993 | Sugiura et al. |
| 5,338,844 A | 8/1994 | Sugiura et al. |
| 5,684,205 A | 11/1997 | Norman et al. |
| 6,087,401 A | 7/2000 | Koyama et al. |

FOREIGN PATENT DOCUMENTS

| | | | |
|---|---|---|---|
| EP | 0131441 | * | 7/1984 |
| JP | 62-44 | | 1/1987 |
| JP | 7-233142 | | 9/1995 |
| JP | 9-169780 | | 6/1997 |

OTHER PUBLICATIONS

Rossi et al, Proc.Natl.Acad.Sci., vol. 94, pp. 746–750, 1997.*
Rossi et al, The Journal of Biological Chemistry,, vol. 271, pp. 32192–32196, 1996.*
Ulrike Zabel et al., DNA Binding of Purified Transcription Factor NF–KB, The Journal of Biological Chemistry, vol. 266, No. 1, Issue of Jan. 5, pp. 252–260, 1991.
Antonio Rosi et al., HSF Induction by Cyclopentenone Prostaglandins Prevents NF–KB Activation in Human Cells: Implications in the Control of Virus Infection., May 1–5, 1996, p. 255.
M. Gabriella Santoro et al., Prostaglandins with Antiproliferative Activity Induce the Synthesis of Heat Shock Protein in Human Cells., Proc. Natl. Sci. USA, vol. 86, pp. 8407–8411, Nov. 1989.
M. Gabriella Santoro et al., Induction of HSP70 by Prostaglandins, pp. 27–44 (1990).
H. Becker et al., Analysis of Proteins that Interact with the IL–2 Regulatory Region in Patients with Rheumatic Diseases, Clinical Exp. Immunol 195, 99; 325–330 91995).
Dimitris Thanos and Tom Maniatis, NF–KB: A Lesson in Family Values, Cell, vol. 80, 529–532, Feb 24, 1995.
Stefan Grimm and Patrick A. Baeuerle, The Inducible Transcription Factor NF–kB: Structure–Function Relationship of its Protein Submits Biochem,J, 290, 297–308 (1993).
Antero Salminen et al, Alteration of Transcription Factor Binding in the Ischemic Rat Brain, Biochemical and Biophysical Research Communications, pp. 939–944, vol. 212, No. 3, 1995.
Albert S. Baldwin, Jr., The NF–kB and Ik Proteins: New Discoveries and Insights, Annu. Rev. Immunol, 1996. 14:649–81.
Michael J. Lenardo et al., NF–kB: A Pleiotropic Mediator of Inducible and Tissue–Specific Gene Control, Cell, vol. 58, 227–229, Jul. 28, 1989.
Carmela Rozera et al., Inhibition of HIV–1 Replication by Cyclopetenone Prostaglandins in Acutely Infected Human Cells, The American Society for Clinical Investigation, Inc., vol. 97, No. 8, Apr. 1996, 1795–1803.
Carla Amici et al., Aspirin Enhances Thermotolerance in Human Erythroleukemic Cells: An Effect Associated with the Modulation of the Heat Shock Response, Cancer Research 55, 4452–4457, Oct. 1, 1995.
Patrick A. Baeuerle and Thomas Henkel, Function and Activation of NF–kB in the Immune system, Annu. Rev. Immunol, 1994, 12: 141–79.
Myers et al., 1996, "An improved preparation of highly enantiomerically enriched (R)–(+)–4–tert–butyldimethylsiloxy–2–cyclopenten–1–one". Tetrahedron Lett. 37(18):3083–86.

* cited by examiner

Primary Examiner—Sreeni Padmanabhan
(74) Attorney, Agent, or Firm—Pennie & Edmonds LLP

(57) ABSTRACT

2-Cyclopenten-1-one and its derivatives comprising the cyclopentenone nucleus as inhibitors of the NF-kB factor, with anti-inflammatory, anti-proliferative, immunosuppressive, cytoprotective and antiviral activity, the substituents being selected among the ones which do not affect the NF-kB inhibitory activity. Further the cyclopentenone derivative is a cyclopentenone compound which does not have two adjacent aliphatic side chains or a prostaglandin.

19 Claims, 1 Drawing Sheet

2-CYCLOPENTEN-1-ONE AS INHIBITORS OF THE NF-KB FACTOR

This application is a 371 of PCT/EP97/06930 filed Dec. 11, 1997.

FIELD OF INVENTION

The present invention relates to 2-cyclopenten-1-one and its derivatives as inhibitors of the transcription factor Nuclear Factor-kappaB (NF-κB). In particular the invention relates to 2-cyclopenten-1-one and its derivatives comprising the cyclopentenone nucleus as inhibitors of the NF-κB factor with anti-inflammatory, antiproliferative, immunosuppressive, cytoprotective and antiviral activity.

BACKGROUND OF THE INVENTION

NF-κB (Nuclear Factor-κB) is an eucariotic transcription factor of the rel family, which is normally located in the cytoplasm in an inactive complex, whose predominant form is a heterodimer composed of p50 and p65 subunits, bound to inhibitory proteins of the IκB family, usually IκB-alpha (D. Thanos and T. Maniatis, and Cell 80:529–532, 1995).

NF-κB is activated in response to different stimuli, among which phorbol esters, inflammatory cytokines, UV radiation, bacterial and viral infections. Stimulation triggers the release of NF-κB from IκB in consequence of the phosphorylation and the following degradation of the IκB-alpha protein (P. A. Baeuerle and T. Henkel, Annu. Rev. Immunol. 12: 141–179, 1994). Once it is activated, NF-κB translocates to the nucleus where it binds to DNA at specific κB-sites and induces the transcription of a variety of genes encoding proteins involved in controlling the immune and inflammatory responses, among which a variety of interleukins, the tumor necrosis factor alpha, the NO synthase and the cyclo-oxigenase 2 (S. Grimm and P. A. Baeuerle, Biochem. J. 290: 297–308, 1993). Accordingly, NF-κB is considered an early mediator of the immune and inflammatory responses and it is involved in the control of cell proliferation and in the pathogenesis of various human diseases, among which rheumatoid arthritis (H. Beker et al., Clin. Exp. Immunol. 99: 325, 1995), ischemia (A. Salminen et al. Biochem. Biophys. Res. Comm. 212: 939, 1995), arteriosclerosis (A. S. Baldwin. Annals Rev. Immunol. 14: 649, 1996), as well as in the pathogenesis of the acquired immunodeficiency syndrome (AIDS), due to the enhanced human immunodeficiency virus (HIV-1) transcription in the presence of activated NF-κB. The increase of HIV-1 virus RNAs transcription by NF-κB is caused by the presence of κB-sites in the (LTR) (Long Terminal Repeats) sequences of the virus genome (M. J. Lenardo and D. Baltimore, Cell 58: 227–229, 1989).

It is also known that prostaglandins (PGs) are a class of naturally occurring cyclic 20-carbon fatty acids that are synthetized by various types of eukaryotic cells in response to external stimuli and play an important role in a variety of physiological responses. Since their discovery, PGs were shown to act as microenvironmental hormones and intracellular signal mediators and to control a large number of physiological and pathological processes, including cell proliferation and differentiation, the immune response, inflammation, cytoprotection and the febrile response. In particular, type A and J PGs, which possess a cyclopentenonic structure, are strong inhibitors of virus replication ("Stress Proteins: Induction and Function" Schlesinger M J, Garaci E., Santoro M. G. ed.s, Springer-Verlag, Heidelberg-Berlin, 27–44, 1990). Particularly, it has been recently demonstrated that cyclopentenonic prostaglandins inhibit HIV-1 virus replication, by blocking the viral RNAs transcription (C. Rozera et al. J. Clin. Invest. 97: 1795, 1996).

It is also known that the Heat Shock Proteins (HSPs), also called stress proteins (Proc. Natl. Acad. Sci. USA 86, 8407–8411, 1989), are a family of polypeptides synthetized by eukaryotic and prokaryotic cells in response to heat shock or other kinds of environmental stresses. The HSPs are encoded by a cellular subgroup of genes, identified as stress genes.

The authors have shown that the cyclopentenone prostaglandin PGA inhibits the activation of NF-κB in human cells by inhibiting the phosphorylation and degradation of the inhibitory IκB-alpha protein (A. Rossi, G. Elia and M. G. Santoro, Cold Spring Harbour, N.Y. 1–5 May, 1996, Abstract p. 255).

The authors have also recently shown that inhibition of NF-κB activation is one of the molecular mechanisms used by cyclopentenonic prostaglandins to cause a selective and reversible block of HIV-1 virus RNAs transcription.

SUMMARY OF THE INVENTION

It has now been found that 2-cyclopenten-1-one, the structure constituting the center nucleus of PGA, possesses an activity which is analogous to PGA, that is, it is able to inhibit NF-κB activation, even though it does not contain the corresponding acid function and aliphatic lateral chains. Therefore it is found that the lateral chains, which are present in the PGA with their substituents and double bonds, in particular the acid function, which implies the fatty acid nature of prostaglandins, can be eliminated without substantially modifying the herein above described specific activity. It is also found that the alpha, β-unsatured carbonyl group in the cyclopentenone ring is the key structure necessary for NF-κB inhibition.

Furthermore it has been found that the inhibition of NF-κB by the cyclopentenone group is related to the ability to activate the HSF transcription factor (Heat Shock Transcription Factor), which is responsible for the synthesis of HSPs (Heat Shock Proteins).

In view of the fact that NF-κB inhibition is associated with HSF activation, it is evident that molecules containing the cyclopentenone nucleus, which is active in inhibiting NF-κB, will be inducers of the HSF factor and therefore they will be inducers of heat shock proteins. It is therefore an object of the present invention the 2-cyclopenten-1-one, and its substituted derivatives comprising the cyclopentenone nucleus, as inhibitors of NF-κB, the substituents being selected among the ones which do not affect the NF-κB inhibitory activity.

Another object of the present invention is the 2-cyclopenten-1-one and its pharmacologically acceptable derivatives as inhibitors of NF-κB.

Another object of the invention is the 2-cyclopenten-1-one and its derivatives as inhibitors of NF-κB with anti-inflammatory, anti-proliferative, immuno-suppressive, cytoprotective and antiviral activity.

A further object of the invention are pharmaceutical compositions comprising 2-cyclopenten-1-one and/or its pharmaceutically acceptable derivatives to make medicaments with anti-inflammatory, anti-proliferative, immuno-suppressive, cytoprotective and antiviral activity. In particular with antiviral activity against the HIV-1 virus and viruses whose transcription is controlled by NF-κB, including herpesviruses.

DETAILED DESCRIPTION OF THE INVENTION

The 2-cyclopenten-1-one is a known product, which can be synthetized according to the process described in Beilstein (Daene, Eder, A. 539 [1939] 207, 211).

Figure 1A:
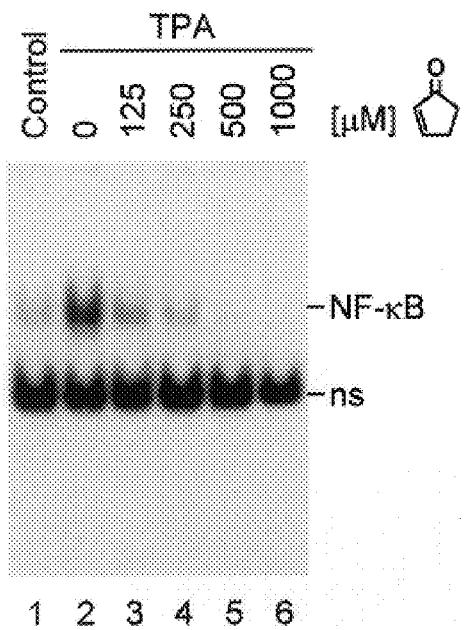
FIG. 1A shows the dose-dependent inhibition of NF-κB activation by 2-cyclopenten-1-one.

According to the present invention 2-cyclopente-1-one, preferably in concentrations ranging between 100 and 500 uM, is able to inhibit NF-κB activation in human cells (FIG. 1A).

Inhibition tests have been carried out in type T lymphoid human cells (Jurkat cell line), as well as in other human cell lines. NF-κB activation was stimulated with 12-o-tetradecanoyl-phorbol-13-acetate (TPA). 2-Cyclopenten-1-one was also effective in inhibiting NF-κB activation after other types of stimulation, including stimulation by tumor necrosis factor alpha or viral infection, and in different types of human cells (data not shown). It is demonstrated that NF-κB inhibition is associated with the activation of HSF factor (FIG. 1B).

Figure 1C:
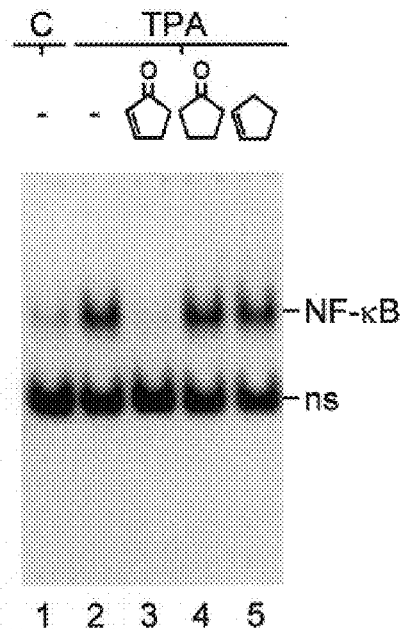
FIG. 1C shows the specificity of the chemical structure which is responsible for NF-κB inhibition.
Figure 1B:
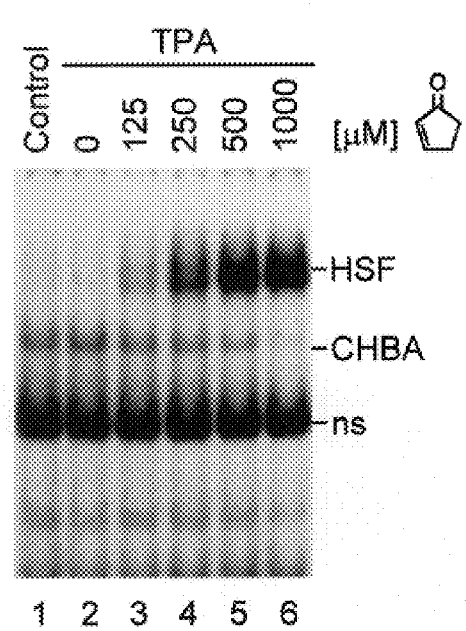
FIG. 1B shows the activation of the HSF factor (Heat Shock Transcription Factor) by 2-cyclopenten-1-one in association with NF-κB inhibition.
Figure 1D:
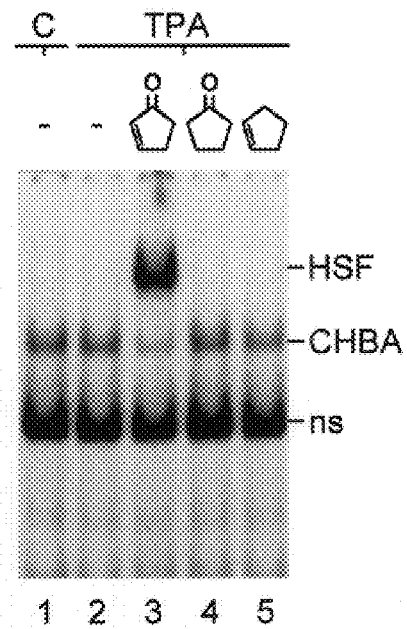
FIG. 1D shows the specificity of the chemical structure which is responsible for HSF activation.

It is also proved that the ability to inhibit the NF-κB factor is specific for 2-cyclopenten-1-one, whereas similar molecules, such as cyclopentanone and cyclopentene, do not inhibit NF-κB (FIG. 1C) and do not activate HSF (FIG. 1D).

Based on these results it is possible to use 2-cyclopenten-1-one, as well as its pharmaceutically acceptable derivatives, as active substances to produce medicaments, in particular medicaments having activity in inhibiting the NF-κB factor, and in particular:

- anti-inflammatory and immunosuppressive medicaments, in view of the role of NF-κB in stimulating the inflammatory and immune responses;
- cytoprotective medicaments, in view of the role of NF-κB in ischemia and oxidative damages;
- antiproliferative medicaments, in view of the role of NF-κB in cell proliferation;
- antiviral medicaments, in view of the role of NF-κB in activating the viral RNAs transcription.

The following examples are reported to illustrate the invention. They should be considered in any case non limiting the scope of the invention itself.

The reagents used in the examples, including 2-cyclopenten-1-one, cyclopentene, cyclopentanone and 12-o-tetradecanoyl-phorbol-13-acetate (TPA), were products of Sigma Aldrich. $^{32}$P e $^{35}$S were produced by AMERSHAM. Fetal calf serum and cellular culture media were produced by GIBCO.

EXAMPLE 1

The effect of the treatment with 2-cyclopenten-1-one on NF-κB activation by TPA has been tested in Jurkat cells by using the procedures described hereinbelow and shown in FIG. 1.

Dose-response Effect

The cells were prepared according to the method described in C. Amici et al. (Cancer Research 55, 4452–4457, 1995).

The cells were treated with 2-cyclopenten-1-one at different concentrations (125–100 uM) for 1 hour and then were stimulated with TPA (25 ng/ml).

After 3 hours the whole-cell extracts were prepared and subjected to EMSA (Electrophoretic Mobility Shift Assay) as described for NF-κB in U. Zabel et al. (J. Biol. Chem. 266: 242, 1991) and HSF in C. Amici et al. (Cancer Res. 55: 4452, 1995), to determine NF-κB and HSF activation respectively. The positions of the complex NF-κB-DNA (NF-κB) and the non-specific binding (ns) are indicated in FIG. 1A.

The positions of the complex HSF-DNA (HSF), the HSF-DNA constitutive activity (CHBA) and the proteins-DNA non-specific interactions (ns) are indicated in FIG. 1B. The line "control" indicates the non-TPA-stimulated cells as a control of non-activated NF-κB.

As evident, 2-cyclopenten-1-one is able to inhibit NF-κB activation by TPA even at the lower concentration of 125 uM. At the concentration of 500 um the NF-κB band is absent (FIG. A). In correlation with NF-κB inhibition, in the same samples it is evident the activation of HSF starting from the concentration of 125 uM (FIG. 1B).

Specificity of the Inhibitory Effect (FIG. 1C)

The cells were treated for 1 hour with the same concentration (500 uM) of: 2-cyclopenten-1-one (line 3), cyclopentanone (line 4) or cyclopentene (line 5), and then were stimulated with TPA (25 ng/ml). C represents the non-TPA-stimulated control. After 3 hours the whole-cell extracts were prepared and subjected to EMSA to verify the activation of NF-κB (FIG. 1C) and of HSF (FIG. 1D) respectively.

As evident, (i) TPA activates NF-κB (line 2); (ii) 2-cyclopenten-1-one inhibits TPA-induced NF-κB activation (line 3); cyclopentanone (line 4) and cyclopentene (line 5) do not inhibit NF-κB activation.

In addition, as shown in FIG. 1D, in the same samples inhibition of NF-κB, shown in FIG. 1C, is associated with activation of HSF. These results clearly show that the alpha, β-unsaturated carbonyl group is the key structure trigging HSF activation and its presence is necessary to inhibit NF-κB activation.

What is claimed is:

1. A method of treating an inflammatory disorder in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

2. The method of claim 1, wherein the 2-cyclopenten-1-one or a pharmaceutically acceptable derivative thereof is administered to provide a concentration ranging between 100 and 500 μM.

3. A method of treating an immune disorder in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

4. The method of claim 3 wherein the 2-cyclopenten-1-one or a pharmaceutically acceptable derivative thereof is administered to provide a concentration ranging between 100 and 500 μM.

5. A method of treating a disorder in a subject, said disorder involving cell proliferation comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains or a prostaglandin.

6. The method of claim 5, wherein the 2-cyclopenten-1-one or a pharmaceutically acceptable derivative thereof is administered to provide a concentration ranging between 100 and 500 μM.

7. A method of treating ischemia in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

8. The method of claim 7, wherein the 2-cyclopenten-1-one or a pharmaceutically acceptable derivative thereof is administered to provide a concentration ranging between 100 and 500 μM.

9. A method of treating oxidative cell damage in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

10. The method of claim 9, wherein the 2-cyclopenten-1-one or a pharmaceutically acceptable derivative thereof is administered to provide a concentration ranging between 100 and 500 μM.

11. A method of treating arteriosclerosis in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

12. The method of claim 11 wherein the 2-cyclopenten-1-one or a pharmaceutically acceptable derivative thereof is administered to provide a concentration ranging between 100 and 500 μM.

13. A method of treating rheumatoid arthritis in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

14. The method of claim 13, wherein the 2-cyclopenten-1-one or a pharmaceutically acceptable derivative thereof is administered to provide a concentration ranging between 100 and 500 μM.

15. A method of treating a viral infection in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

16. The method of claim 15 wherein the 2-cyclopenten-1-one or a pharmaceutically acceptable derivative thereof is administered to provide a concentration ranging between 100 and 500 μM.

17. The method of claim 15 or 16, wherein the viral infection is an HIV-1 infection.

18. A method of treating AIDS in a subject comprising administering to said subject a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

19. The method of claim 18, wherein the 2-cyclopenten-1-one or a pharmaceutically acceptable derivative thereof is administered to provide a concentration ranging, between 100 and 500 μM.

\* \* \* \* \*